United States Patent [19]

Haughton

[11] Patent Number: 4,932,271

[45] Date of Patent: Jun. 12, 1990

[54] MOLTEN METAL SAMPLING DEVICE

[75] Inventor: Gary H. Haughton, Burlington, Canada

[73] Assignee: Evacuo Enterprises Limited, Hamilton, Canada

[21] Appl. No.: 240,506

[22] Filed: Sep. 6, 1988

[30] Foreign Application Priority Data

Sep. 9, 1987 [GB] United Kingdom ............... 8721185

[51] Int. Cl.⁵ ............................................. G01N 1/10
[52] U.S. Cl. .............................. 73/864.53; 73/DIG. 9
[58] Field of Search .................... 73/864.51–864.59, 73/864.63, DIG. 9; 266/99

[56] References Cited

U.S. PATENT DOCUMENTS

| 3,452,602 | 7/1969 | Hackett | 73/DIG. 9 |
| 3,877,309 | 4/1975 | Hance | 73/DIG. 9 |
| 4,067,242 | 1/1978 | Judge | 73/DIG. 9 |
| 4,211,117 | 7/1980 | Cure | 73/DIG. 9 |

FOREIGN PATENT DOCUMENTS 1526144 4/1968 France ............................. 73/864.55

Primary Examiner—Robert R. Raevis
Attorney, Agent, or Firm—Shoemaker and Mattare, Ltd.

[57] ABSTRACT

A holder for a molten metal sampling device includes a thick-walled metallic pipe having a lower portion defining an internal guidance chamber, and an upper portion receiving an retaining a sampling device. An opening is provided in the pipe such as to make it define an angle with respect to the axis of the pipe. A closure element is provided, having a density such that it will seek to float upwardly in molten metal being sampled. A retaining element urges the closure element against the opening to close it. The retaining element is located and has a composition such that it will readily melt upon contact with the molten metal.

9 Claims, 8 Drawing Sheets

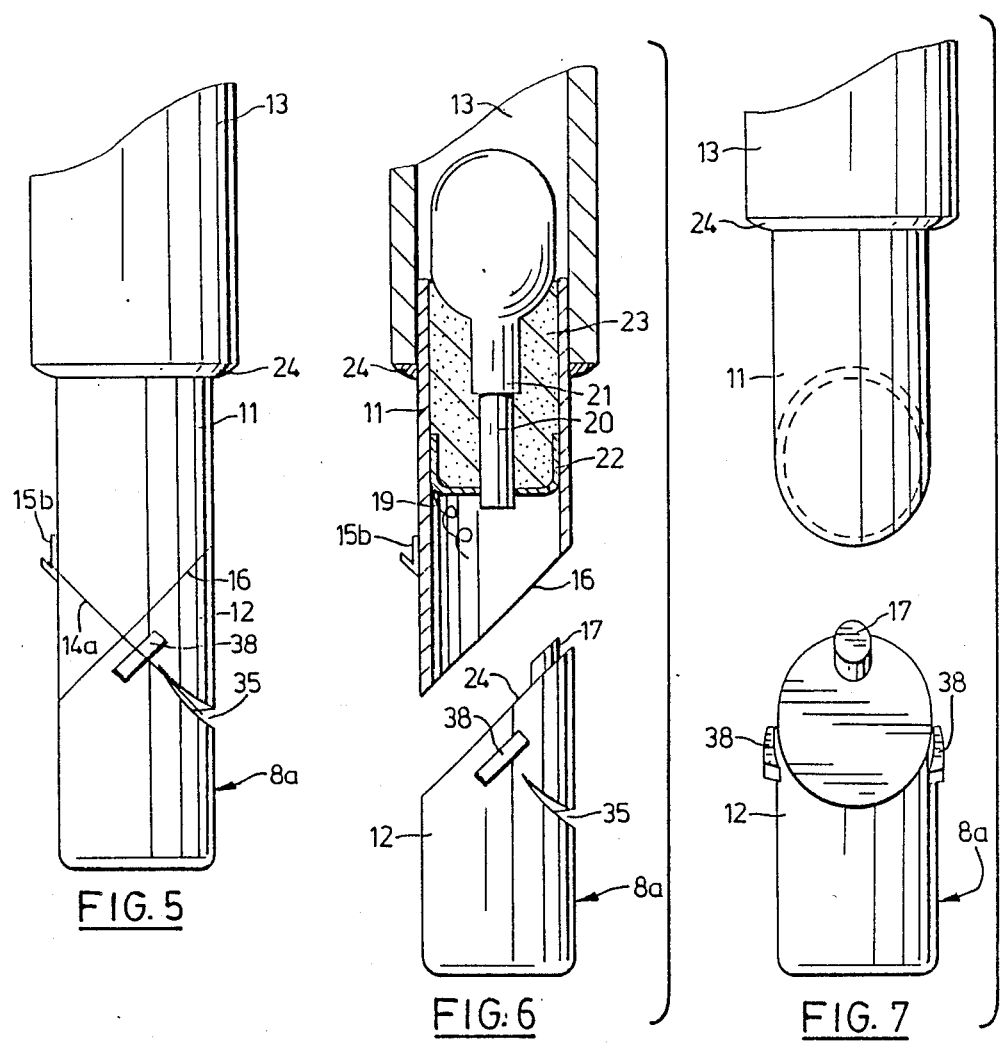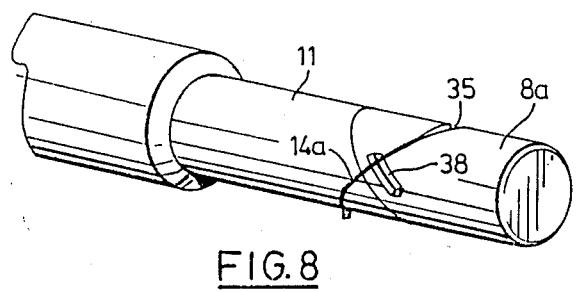

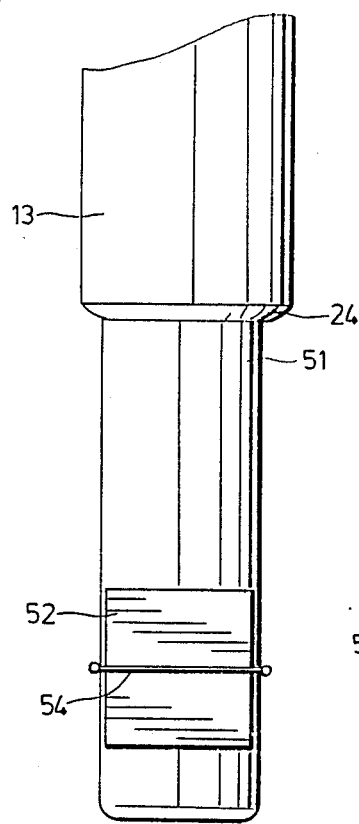 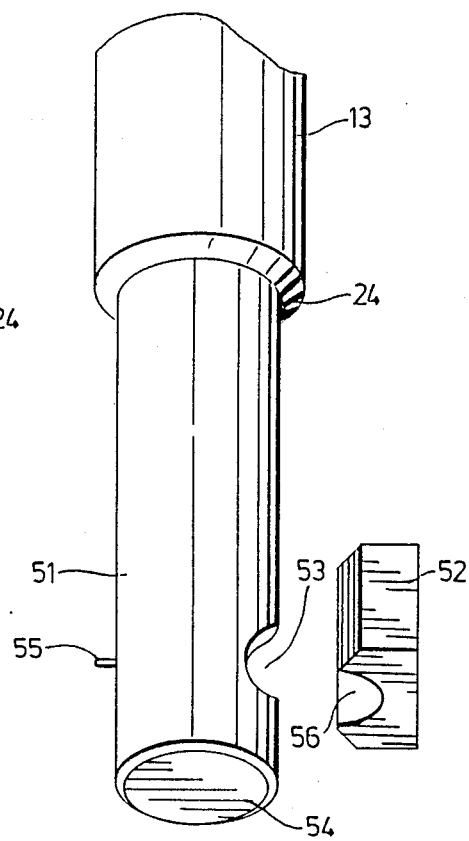
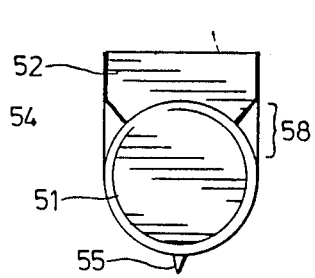 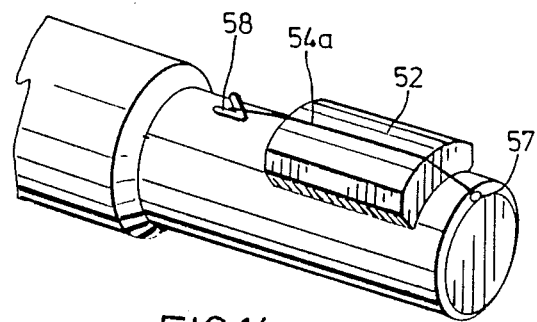
FIG. 11  FIG. 12
FIG. 13  FIG. 14

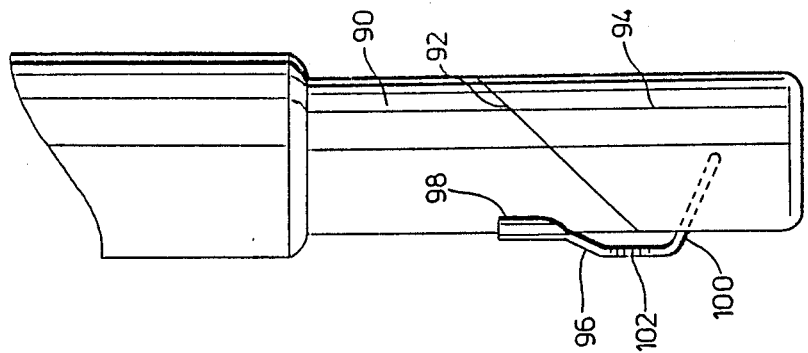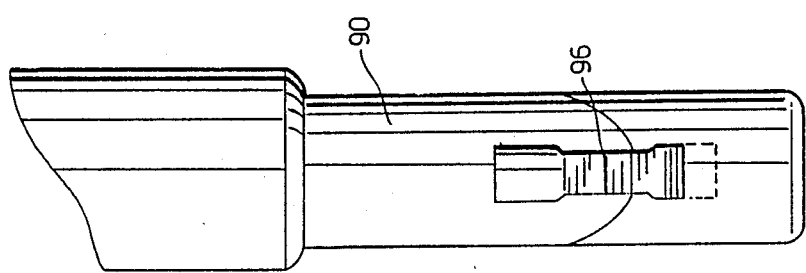

MOLTEN METAL SAMPLING DEVICE

The present invention relates to molten metal sampling devices, especially to such devices with a non-diluting and non-contaminating protection cap and entrance system.

BACKGROUND OF THIS INVENTION

Prior samplers have been designed with a capping and entrance system that melted along with and into the molten material being sampled. This caused a source of undesirable contaminants to flow into the actual sample chamber. The prior method also allowed elements contained in the capping system to cause a diluting effect on similar elements contained in the molten batch material.

The location being sampled may contain extremely low (typically, 10 to 50 ppm) values of certain elements, for example, C, S, Mn, $0_2$, H and N, that must be accurately analyzed in order to produce a high quality product. At these minute ranges, any outside contamination or dilution can cause a significant error in accurate analysis.

Patents representative of the prior art in this area are as follows:

U.S. Pat. No. 4,428,245, issued Jan. 31, 1984 to Nakamura et al;
U.S. Pat. No. 4,007,641, issued Feb. 15, 1977 to Kelsey;
U.S. Pat. No. 4,557,152, issued Dec. 10, 1985 to Plessers et al:
U.S. Pat. No. 4,646,578, issued Mar. 3, 1987 to Lawrenz et al;
U.S. Pat. No. 4,170,139, issued Oct. 9, 1979 to Narita et al;
U.S. Pat. No. 4,250,753, issued Feb. 17, 1981 to Collins;
U.S. Pat. No. 4,140,019, issued Feb. 20, 1979 to Falk;
U.S. Pat. No. 4,112,772, issued Sept. 12, 1978 to McDevitt;
U.S. Pat. No. 4,037,478, issued Jul. 26, 1977 to Cure;
U.S. Pat. No. 4,002,073, issued Jan. 11, 1977 to Collins;
U.S. Pat. No. 3,332,288, issued Jul. 24, 1967 to Mladenovich;
U.S. Pat. No. 3,693,449, issued Sept. 26, 1972 to Collins;
U.S. Pat. No. 4,051,732, issued Oct. 5, 1979 to Falk;
U.S. Pat. No. 3,859,857, issued Jan. 14, 1975 to Falk;

GENERAL DESCRIPTION OF THIS INVENTION

The prior art problems discussed above are overcome in the present invention by using a novel form of capping and entrance system that will not contaminate or dilute the obtained sample. The cap is rapidly released from the sampling device and simply floats away.

The non-diluting/non-contaminating quick release feature of the present invention has the following advantages over known prior art:

1. The quick-release cap and entry system does not become part of the molten metal being sampled. Only clean metal at the location of immersion is transferred to the sample cavity, where it is quickly brought to a solid state.
2. The quick-release feature of the capping system will prevent any foreign substances, for example, slag coverings, from advancing through the entry system and into the sample chamber, until the probe or contained capsule has been completely immersed into the actual area of metal that will produce the most accurate and representative test sample. Once immersed via a lance, holding pipe or other suitable device, the cap quickly is moved or floats upwards and out of the way of the entrance, thus permitting the molten metal to flow rapidly and continuously into the sample chamber, where the metal is sufficiently solidified to produce a representative metal sample.

More particularly, this invention in one aspect provides a holder for a molten metal sampling device, comprising:

a cylindrical pipe which is elongated in a given direction, the pipe having an upper portion and a lower portion, the lower portion defining an internal guidance chamber and having an opening lying in a plane making an oblique angle with said given direction, the opening communicating with the guidance chamber, the upper portion being adapted to receive and retain the molten metal sampling device in such a way that molten metal in the guidance chamber can be sampled by the sampling device, a cylindrical, ceramic closure element for said opening, the closure element having a density such that it will seek to float upwardly in molten metal being sampled, the closure element having substantially the same diameter as the said pipe and being substantially coaxial therewith, and a retaining element urging the closure element against the opening to close the same, the retaining element having a configuration, location and composition such that it will readily fail upon contact with the molten metal.

GENERAL DESCRIPTION OF THE DRAWINGS

Several embodiments of this invention are illustrated in the accompanying drawings, in which like numerals denote like parts throughout the several views, and in which:

FIGS. 5, 6, 7 and 8 are views of a second embodiment of this invention, corresponding to the views of FIGS. 1, 2, 3 and 4, respectively:

FIG. 11 is an elevational view of a fifth embodiment of this invention;

FIG. 12 is a perspective view of the embodiment of FIG. 11, with the parts in exploded relation;

FIG. 13 is a bottom view of the embodiment of FIGS. 11 and 12;

FIG. 14 is a perspective view of the embodiment of FIGS. 11, 12 and 13;

Figure 18C:
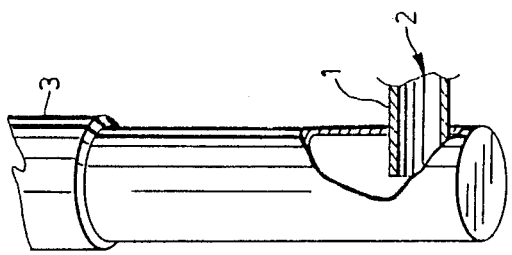
Figure 18B:
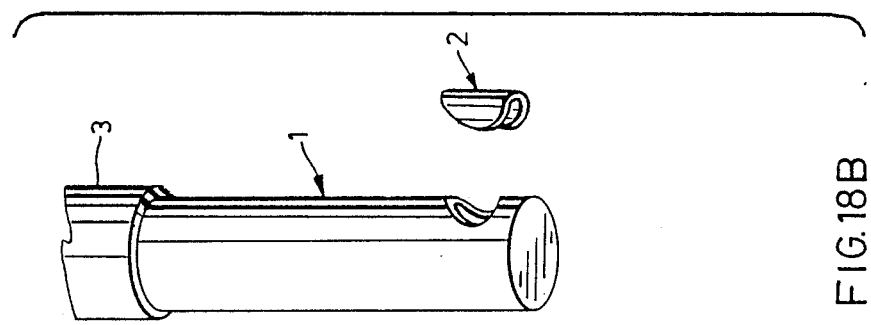
Figure 18A:
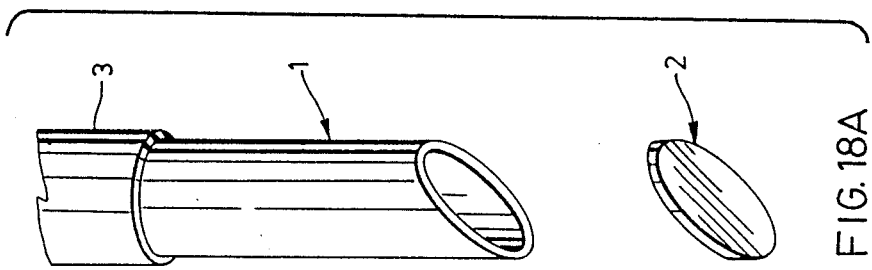

FIG. 18 part A and B are somewhat schematic views of two approaches to solving the problems set forth earlier, seen in perspective; and FIG. 18 part C is a sectional view showing schematically a third approach.

Figure 19:
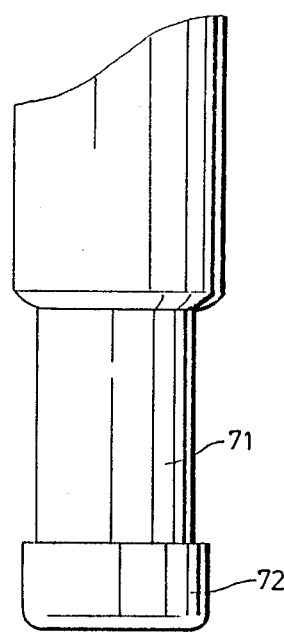
Figure 20:
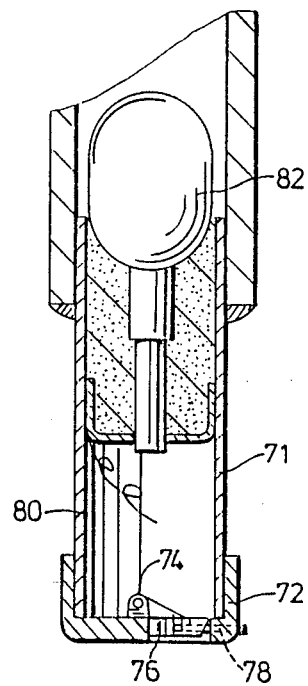
Figure 21:
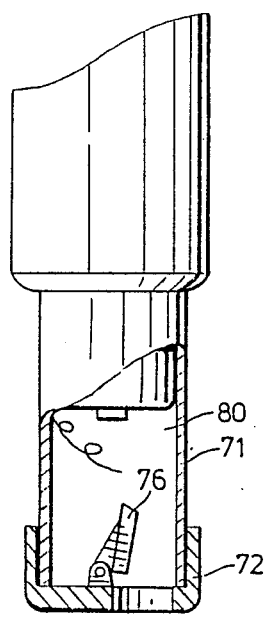
Figure 22:
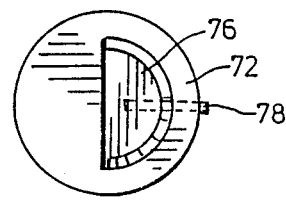
Figure 23:
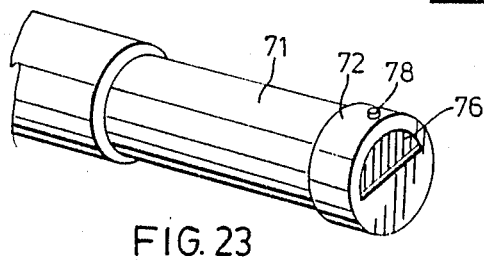
Figure 24:
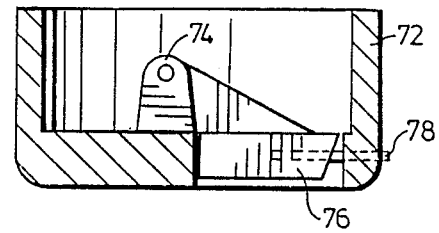

FIG. 19 is an elevational view of a further embodiment of this invention;

FIG. 20 is a vertical sectional view through the embodiment of FIG. 19, with a closure in the closed position;

FIG. 21 is a part axial sectional view showing the closure in the open position;

FIG. 22 is a bottom view of the embodiment of FIG. 19;

FIG. 23 is a perspective view of the embodiment of FIG. 19;

FIG. 24 is a cross-sectional view, to a larger scale, of the closure cap at the bottom of the embodiment shown in FIG. 19; and FIGS. 25 and 26 are two elevational views of a further embodiment of this invention.

DETAILED DESCRIPTION OF THE DRAWINGS

Referring to FIG. 18, each of the sampling devices shown has three essential components 1, 2 and 3. Component 1 is a guidance chamber tube, component 2 is a quick-release cap, and component 3 is a protective sleeve. Each of these components will be discussed in turn:

Component 1

(a) The actual guidance chamber tube usually is made of thick-walled metal, refractory, ceramic or composite material that is unaffected by the molten metal being sampled, and will not become part of the sampled material.

(b) The dimensions of the guidance chamber, and the addition of a suitable deoxidant (Al, Zr, Ti) will vary with the particular area being tested, for example, vessel, ladle, tundish or mold, and also with the type of metal being tested, e.g. killed, semi-killed, rimmed, ferrous or non-ferrous molten metals.

(c) The location, configuration and/or angle of position of the quick-release cap may vary with the application and the angle of immersion of the sampling device.

(d) For special applications, such as in hazardous areas, the guidance chamber may be wrapped or coated with an inert, non-boiling material.

(e) The wall thickness of the guidance chamber material may also vary with the application; for example the temperature of molten material, depth of immersion, length of immersion time, slag conditions, etc.

(f) The guidance chamber, as well as the other components described below, may be coated with a salt compound, a lime based compound, or similar material which will evolve substantial quantities of gas upon being immersed in the molten metal. The gas thus evolved has the effect of preventing the adhesion of slag to the various parts, as the unit is passing down through the slag layer.

Component 2

(a) The quick-release cap, in one embodiment, can be made of a material lighter in weight than the molten metal to be sampled. This would assure that the protective cap would rapidly float away from the molten metal entrance or mixing chamber upon immersion of the sampling device into the metal to be sampled. Depending on the application, the capping material may be composed of refractory material, aluminum, ceramic, hollow material, cladded material, composite material, or other suitable material of construction.

(b) The thickness and shape of the cap varies with the application.

(c) Depending on the application, the cap may be held in position on the component 1 prior to immersion using a variety of materials, including adhesives, tapes of various substances, metal wires or bands, clips, or any other appropriate means that permits proper protection and the prevention of metal entry into the guidance chamber 1 during the immersion phase, and also permits quick release, once in position to receive the molten material to be sampled.

Component 3

(a) A protection sleeve, of cardboard or other suitable material, is used for the containment of the sampling mould and cap.

(b) The length of the kraft paper protection sleeve, or a non-boil sleeve varies depending on the area of application.

Attention is now directed to FIG. 1-4, for a detailed description of a practical form of this invention.

Figures 1, 2, 3:
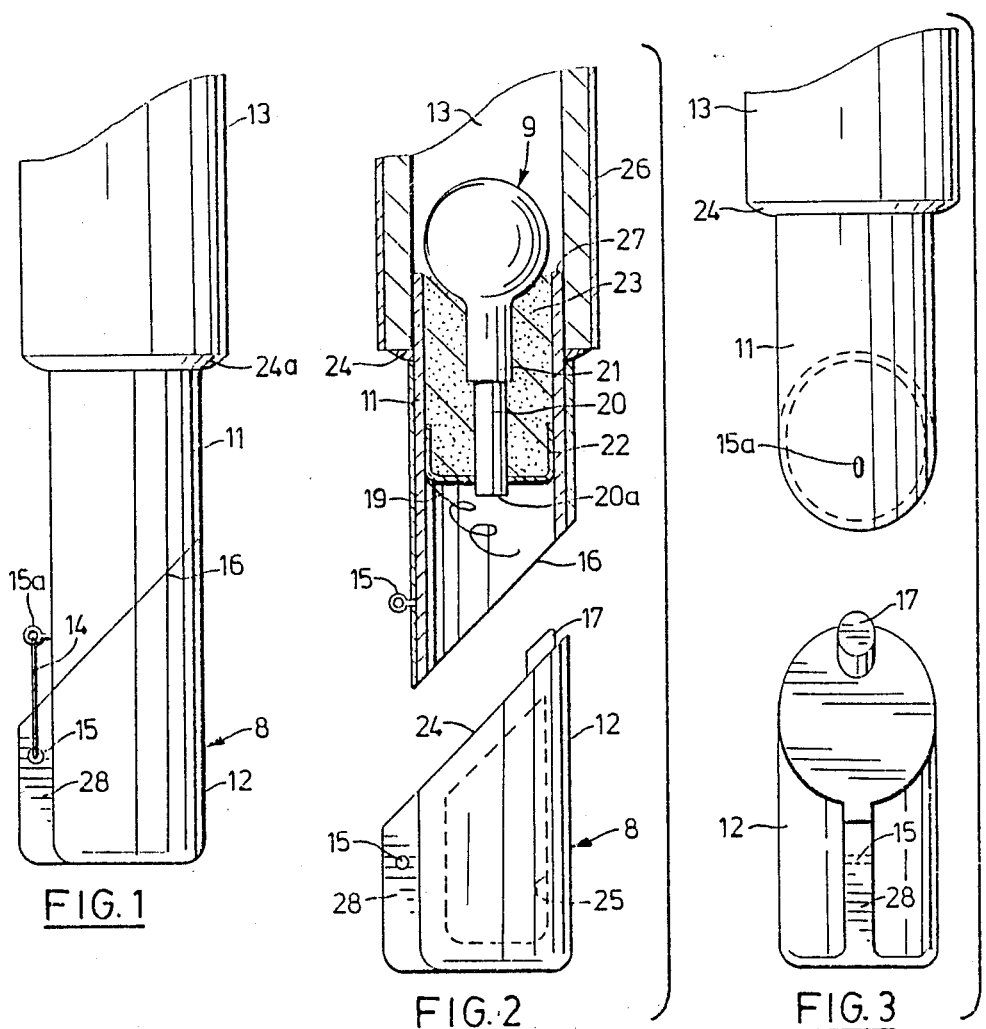
FIG. 1 is an elevational view of the bottom end of a molten metal sampling probe constructed in accordance with one embodiment of this invention.
FIG. 2 is an exploded view of the embodiment of FIG. 1, showing the upper portion in axial section, and the lower portion in elevation.
FIG. 3 is an elevational view of the components shown in FIG. 2, taken from a position 90° rotated from that of FIG. 2.
Figure 4:
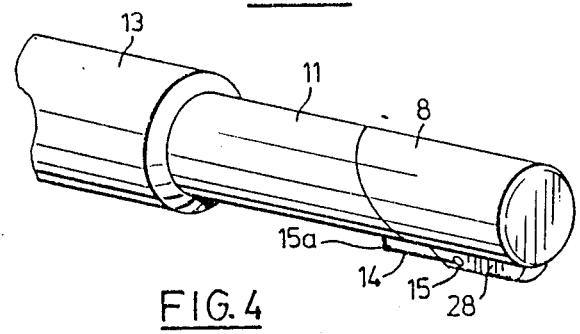
FIG. 4 is a perspective view of the embodiment shown in FIG. 1.

In FIG. 1, 13 represents the protective sleeve, which is preferably covered with a low thermoconductivity, non-boiling coating 26, as seen in FIG. 2. Inserted within the lower end of the sleeve 13 is a thick-walled pipe 11 which has a square cut opening 27 at the top end, and a diagonally cut opening 16 at the bottom. In the particular embodiment shown in FIGS. 1-4, the opening 16 lies in a plane which defines an angle of 45° with the axis of the pipe 11. The pipe 11 may be of metal, metal alloy, refractory or ceramic material.

Contained in the upper portion of the pipe 11 is a molten metal sampling device 9 which is of conventional nature, consisting of two identical mold halves 21 which fit together to define a lollypop-like cavity which will receive the metal sample. In communication with that cavity is a filling pin 20 typically made of high-temperature glass and being open at the bottom end 20a. The filling pin extends downwardly through a central opening in a retainer cup 22. The retainer cup 22 could be replaced by a heavy washer that will not melt on contact with the molten metal. The sampling device 9 is held in place by the provision of a high-temperature packing material 23, in known manner.

Trapped between the retainer cup 22 and the inside wall of the pipe 11 is a strip of the deoxidizing material 19 which may typically be aluminum, zirconium, or titanium.

A closure element is shown generally at 8. It has a substantially cylindrical portion 12 which is shaped as if it were a continuation of the pipe 11. To this end, the closure element 8 has an oblique upper surface 24, making the same angle with the axis of the portion 12 as is made by the opening 16 with respect to the axis of the pipe 11. The closure element 8 may have a hollow interior 25 in order to reduce its weight and increase flotation. Extending leftwardly from the closure element 8, as pictured in FIGS. 1 and 2, is a flange 28 which has substantially a rectangular cross-section. At an intermediate location, the flange 28 has a transverse opening 15, for a purpose which will shortly be explained.

As best seen in FIGS. 1 and 2, the pipe 11 has mounted therein a detent 15a in the form of an eyelet. A fusible wire 14, seen in FIG. 1, extends through the opening 15 and through the detent 15a, in order to urge the closure element 8 against the opening 16 at the bottom of the pipe 11. A further component of the closure means is provided by a pin or projection 17, located in such a way that it can lie within and against the pipe 11 at the uppermost location on the perimeter of the opening 16. This prevents the closure element from sliding obliquely upwardly and rightwardly (as pictured in FIG. 2), thus failing to close the opening 16.

Preferably the fusible wire 14 is made of a metal with a low melting point by comparison with the molten metal to be sampled.

As can be seen in FIGS. 1 and 2, a high temperature sealant 24a is provided at the bottom of the protection sleeve 13.

In operation, the closure element 8 is secured to the bottom of the pipe 11, by lodging the projection 17 inside the uppermost point of the opening 16, and running the wire 14 between the opening 15 and the detent 15a and securely fastening it. When the operator, using the protection sleeve 13, plunges the pipe 11 and the closure element 8 through the slag layer covering the molten metal in a suitable vessel, the heat of the melt quickly fuses the wire 14, which allows the closure element to rotate in counterclockwise motion about the projection 17 where it is "caught" within the upper portion of the opening 16. This opens the opening 16 to allow molten metal to enter the filling pin 20. As the pin is filling, the closure element 8 rapidly floats to the top surface of the melt. Because of the material from which the closure element is made, preferably ceramic or refractory material, it does not melt into and contaminate the metal from which a sample is being taken. The position of the wire 14 is such that it will not contaminate the molten metal flowing into the opening 16.

The operator may extend the sampling device downwardly at an angle (downwardly and to the right for the configurations shown in FIGS. 1 and 2), which will enhance the floatation of the closure element 8. However, it has been found that the sampling device described herein functions satisfactorily at any angle.

It will be understood that the relatively thick-walled pipe 11 will constitute a heat sink for any materials which contact it, particularly if it is made of metal or metal alloy. For example, if the wire 14 were to lie against the pipe 11 at all locations, the melting of the wire 14 by heat of the liquid metal would be delayed and possibly prevented. It is considered important to this invention that at least a portion of the wire 14 be held away from contact with any other parts of the combination which could constitute a heat sink. In the embodiment shown in FIGS. 1 and 2, the wire 14 is spaced away from the pipe 11, and only lies against the flange 28 of the closure element 8. Because the closure element 8 is not made of metal, this contact with the flange 28 will not seriously interfere with the fusing of the wire 14.

It has been found that certain kinds of slag will tend to adhere to the sampling device as it passes through the slag layer. In order to overcome this problem, all exposed parts of the sampler, including the wire 14, may be coated with a slag retardant, or a gas-evolving substance such as a salt solution or calcium carbonate. In connection with the salt solution, it has been found that contact between the salt and the molten metal creates gas which acts as a barrier preventing the slag from contacting the sampler.

Attention is now directed to the embodiment shown in FIGS. 5-8, where the views are identical to the views of FIGS. 1-4, respectively. Identical parts as between the first and second embodiments bear the same numerals, but will not be described unless they touch on the focus of this invention.

As will be immediately noted, the primary difference exhibited by the second embodiment lies in the configuration of the closure element 8a. The closure element 8a has a groove 35 in line with the highest point on the surface 24, and has fuse-release standoffs 38 on opposite sides.

FIGS. 5 and 8 show the way in which a fusible wire 14a wraps around both the closure element 8a and the pipe 11, by passing over the standoffs 38. As best seen in FIGS. 5 and 6, the pipe 11 has affixed thereto a flange 15b around which the wire 14a can be secured. The flange 15b has a J-shape to facilitate snagging the wire 14a.

Thus, the upper part of the drawing in FIG. 6 is identical to the upper part in FIG. 2, except for the flange 15b being different from the eyelet 15a.

By again providing a projection 17 to hook inside the opening 16 at the pipe 11 at the uppermost point, a hinging-rotation of the closure element 8a can be effected as soon as the wire 14a melts. Of course, this rotation and removal of the closure element 8a is enhanced if the operator plunges the lower end of the sampling device into the melt on an angle which would be downwardly and to the right as viewed in FIG. 6.

The closure element 8a may be solid or hollow, depending upon the degree of floatation required.

Figures 9, 10:
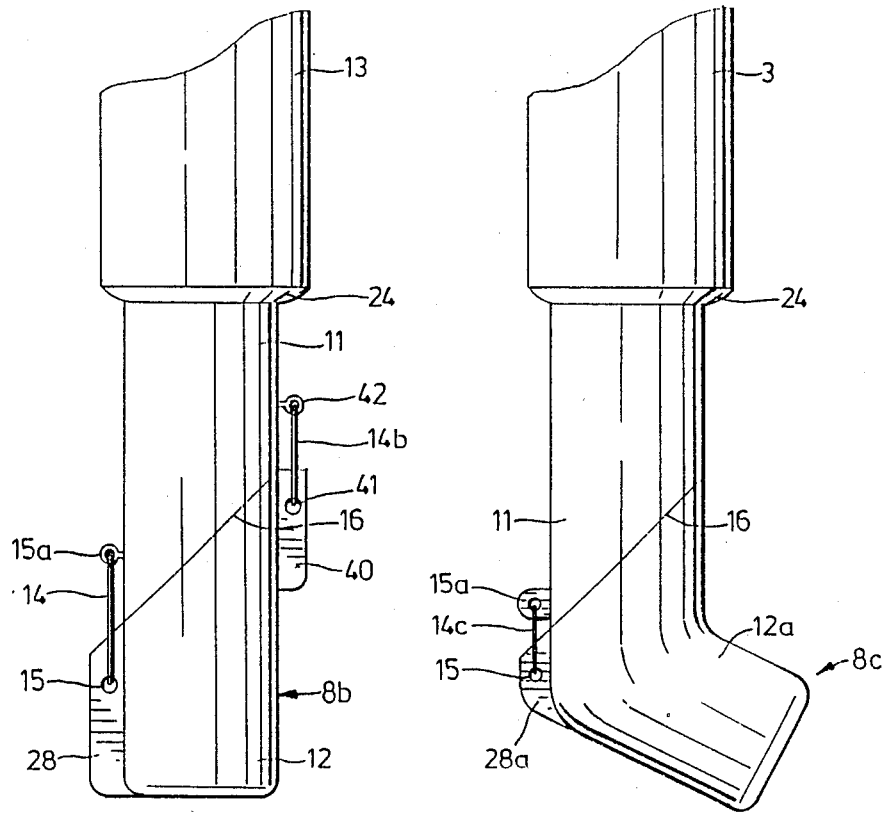
FIG. 9 is an elevational view of a third embodiment of this invention.
FIG. 10 is an elevational view of a fourth embodiment of this invention.

FIG. 9 shows a further embodiment, differing from that of FIG. 1 only in the addition of a further flange 40 with an opening 41, along with a further detent 42 in the shape of an eyelet. A further wire 14b is provided, and is tightened through the eyelet 42 and the opening 41.

The embodiment of FIG. 10 involves the use of a closure element 8c which is bent to the right as seen in the figure, sc that floatation will be enhanced. At the leftward side in FIG. 10, a flange 28a projects outwardly to the left and has an opening 15c. A bracket 15a on the pipe 11 has an opening through which a wire 14c passes. Again, the mode of operation is the same as described for the other embodiments.

Attention is now directed to FIGS. 11-14, for a description of a further embodiment. As can be best seen in FIGS. 12 and 14, the pipe 51 (defining the mixing chamber and its upper portion) has an opening 53 out the right-hand side, while its bottom end is closed by a solid wall 54. The closure element in FIG. 12 is a block of material which is shaped to define a concave cylindrical surface 56 that is complementary to and in contact with the outside wall of the pipe 51.

Located on the pipe 51 at a position diametrically opposed to the opening 53 is an outwardly projecting pin 55 below which a fusible wire 54 can be caught. The fusible wire, as seen in FIG. 13, extends around both the closure element 52 and the pipe 51. It will be noted in FIG. 13 that a portion 58 of the wire on either side is spaced away from anything that could constitute a heat sink and slow down or prevent the fusing of the wire 54.

FIG. 14 shows the same shape for the closure element 52 and the same configuration for the pipe 51. However, it represents a variant in that a wire 54a is tightened between a detent 57 at the bottom of the pipe 51, and a further detent 58 above the location of the closure element 52.

Figures 15, 16:
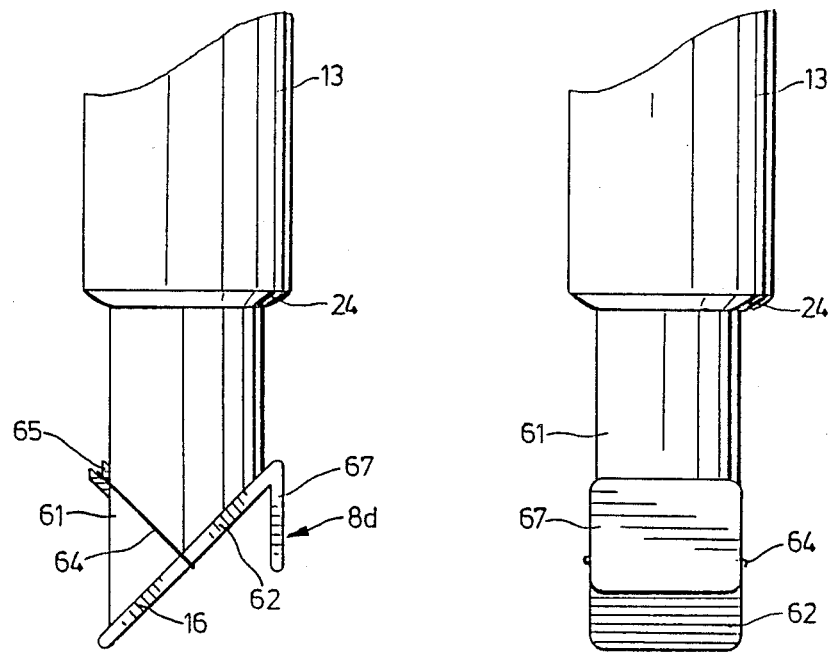
FIG. 15 is an elevational view of a further embodiment of this invention.
FIG. 16 is an elevational view of the embodiment of FIG. 15, taken from a position rotated through 90°.
Figure 17:
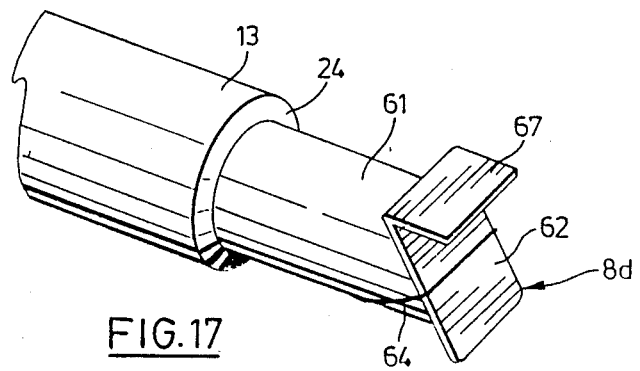
FIG. 17 is a perspective view of the embodiment of FIG. 15.

FIG. 15, 16 and 17 illustrate a further embodiment, in which the pipe 61 again defines a guidance chamber in its upper portion. Its lower end is open obliquely as at 16, similarly to the configuration of FIG. 1. The closure element 8d consists of a first flat portion 62, and a further flat portion 67 extending downwardly at an angle of 45° with respect to the portion 62. A flange 65 is secured to the pipe 61, identically to the flange 15b in FIG. 5. As can be seen, the fusible wire 64 is adapted to wrap under the portion 62 and to be snagged in the brackets 65, thus holding the closure element 8d in position until the wire 64 melts due to the heat of the molten metal.

The closure element 8d could be made from a relatively dense material (such as steel), in which case it would be advisable to secure either to the portion 62 or to the portion 62 a block of low-density buoyant material such as wood or light refractory.

Attention is now directed to FIGS. 19-24, which illustrate a further embodiment of this invention. Parts that are similar to corresponding parts in other embodiments will not be described, in order to avoid repetition. Looking at FIG. 20, the thick-walled pipe 71 has a square-cut bottom end, meaning that it is not cut on an angle. Fitted on the bottom end is a ceramic cap 72 which incorporates a hinge 74 and a hinged flap 76. The flap 76 is initially held in place by the presence of a short rod or wire 78 which projects inwardly from the outside of the cap 72. After immersion in the molten metal to be sampled, contact between the pin 78 and the molten metal causes the pin 78 to fuse or melt, thus releasing the flap 76 to swing upwardly to the position shown in FIG. 21, simultaneously allowing the hot metal to enter the guidance chamber 80 inside the pipe 11. From that location, it can enter the bottom of the sampler 82 (see FIG. 20).

Attention is now directed to FIGS. 25 and 26, which show the final embodiment of this invention. In these figures, the pipe 90 is cut on an angle as shown at 92 in FIG. 26. A solid closure member 94, which may be of ceramic or refractory material, also has a diagonal cut at the top so that it can be received against the angled bottom 92 of the pipe 90. A metallic band 96 is secured by adhesive or other suitable means to the pipe 90, as shown at 98, and has a bottom portion 100 which penetrates into and is buried within the closure member 94. It will be noted that the element 96 includes a portion 102 which is spaced away from the pipe 90, thus allowing the molten metal to dissolve the element 96, thus releasing the closure member 94 so that it can separate from the pipe 90 and allow molten metal to enter the interior of the pipe 90.

It has been found that the following composition will provide a satisfactory material for the cap shown in the figures:
$SiO_2$—27.7 to 37%
$Al_2O_3$—58 to 67%
$MgO$—0.1 to 0.6%
$CaO$—0.1 to 0.3%
$Fe_2O_3$—0.9 to 2.7%
$TiO_2$ 1.7 to 3.0%
Alkali—0.2 to 1.2%

The foregoing material, weighing approximately 58 lbs/cu. ft., can be coated with a refractory wash for added surface strength.

While several embodiments of this invention has been illustrated in the accompanying drawings and described hereinabove, it will be evident to those skilled in the art that changes and modifications may be made therein, without departing from the essence of this invention, as set forth in the appended claims.

The embodiments of the invention in which an exclusive property or privilege is claimed are defined as follows:

1. A holder for a molten metal sampling device, comprising:
   a cylindrical pipe which is elongated in a given direction, the pipe having an upper portion and a lower portion, the lower portion defining an internal guidance chamber and having an opening lying in a plane making an oblique angle with said given direction, the opening communicating with the guidance chamber, the upper portion being adapted to receive and retain the molten metal sampling device in such a way that molten metal in the guidance chamber can be sampled by the sampling device,
   a cylindrical, ceramic closure element for said opening, the closure element having a density such that it will seek to float upwardly in molten metal being sampled, the closure element having substantially the same diameter as the said pipe and being substantially coaxial therewith,
   and a retaining element urging the closure element against the opening to close the same, the retaining element having a configuration, location and a composition such that it will readily fail upon contact with the molten metal.

2. The holder claimed in claim 1, in which the retaining element is a metallic wire wrapped around both the pipe and the closure element, the disposition of the wire being such that at least one portion thereof is spaced away from both the pipe and the closure element, thereby providing a portion which will readily melt without any retardation being caused due to the proximity of a heat-sink or contact therewith.

3. The holder claimed in claim 1, in which the closure element has a projection adapted to lie within the pipe at the uppermost location on said perimeter of the opening, and in which the retaining element is a metallic wire connected in such a way as to urge the closure element upwardly with respect to the pipe.

4. The holder claimed in claim 3, in which the closure element has an external groove and the pipe has a detent means, the wire encircling the join between the pipe and the closure element, the wire lying within said groove and being in contact with said detent, the closure element having at least one outward projection over which the wire passes, thereby lifting a portion of the wire away from contact with either the closure element or the pipe.

5. The holder claimed in claim 3, in which both the closure element and the pipe have detent means between which the wire can be connected in order to draw the closure element into tight engagement with the pipe, the detent means being such that at least a portion of the wire is spaced away from contact with either the closure element or the pipe, the wire being located diametrally opposite the uppermost point of the opening.

6. The holder claimed in claim 1, in combination with a molten metal sampling device, the latter being mounted in the upper portion of the pipe.

7. The holder claimed in claim 1, in which exposed portions of the holder are coated with a material which interferes with the tendency for the slag to adhere to the holder.

8. The holder claimed in claim 7, in which said material is a salt compound.

9. The holder claimed in claim 7, in which said material is a lime-based compound.

* * * * *